(12) United States Patent
Morris

(10) Patent No.: US 10,183,417 B2
(45) Date of Patent: Jan. 22, 2019

(54) ELECTROSURGICAL INSTRUMENT

(71) Applicant: GYRUS MEDICAL LIMITED, Cardiff (GB)

(72) Inventor: David Wyn Morris, Rhondda (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 336 days.

(21) Appl. No.: 14/541,947

(22) Filed: Nov. 14, 2014

(65) Prior Publication Data
US 2015/0069673 A1 Mar. 12, 2015

Related U.S. Application Data

(62) Division of application No. 13/011,512, filed on Jan. 21, 2011.
(Continued)

(30) Foreign Application Priority Data

Feb. 1, 2010 (GB) .................................. 1001645.9

(51) Int. Cl.
*B28B 1/24* (2006.01)
*A61B 18/14* (2006.01)
(Continued)

(52) U.S. Cl.
CPC ................ *B28B 1/24* (2013.01); *A61B 18/14* (2013.01); *A61B 18/148* (2013.01);
(Continued)

(58) Field of Classification Search
CPC ................ B28B 1/24; Y10T 29/49158; Y10T 29/49155; Y10T 29/49124;
(Continued)

(56) References Cited

U.S. PATENT DOCUMENTS 6,168,593 B1   1/2001  Sharkey et al.
6,832,998 B2   12/2004 Goble
(Continued)

FOREIGN PATENT DOCUMENTS

DE    42 37 321 C2      4/1995
DE    102011105404 A1   12/2012
(Continued)

OTHER PUBLICATIONS

May 25, 2010 British Search Report for priority British Application No. 1001645.9.
(Continued)

*Primary Examiner* — Peter DungBa Vo
*Assistant Examiner* — Azm Parvez
(74) *Attorney, Agent, or Firm* — Oliff PLC

(57) ABSTRACT

An electrosurgical instrument is manufactured by presenting an electrode, and attaching a sacrificial portion to the electrode to form a first electrode assembly. An insulating material is molded over the first electrode assembly to form a second electrode assembly, and the second electrode assembly is subjected to a further process which is capable of removing the sacrificial portion without removing the insulating material. The sacrificial portion is removed to form at least one cavity within the electrosurgical instrument.

10 Claims, 3 Drawing Sheets

Related U.S. Application Data

Figure 1:
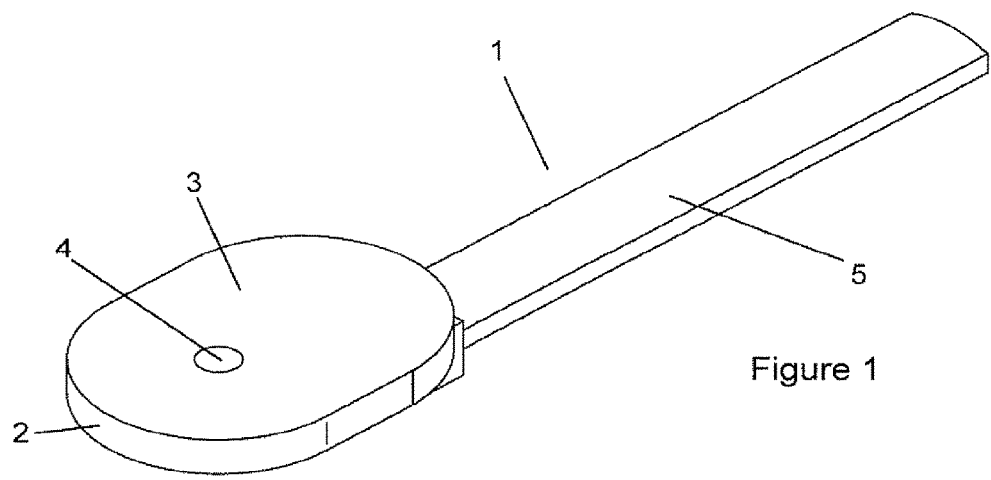

(60) Provisional application No. 61/300,068, filed on Feb. 1, 2010.

(51) Int. Cl.
  *B28B 11/24* (2006.01)
  *A61B 17/00* (2006.01)
  *A61B 18/00* (2006.01)

(52) U.S. Cl.
  CPC ..... *B28B 11/243* (2013.01); *A61B 2017/0088* (2013.01); *A61B 2018/00136* (2013.01); *A61B 2218/002* (2013.01); *Y10T 29/49158* (2015.01)

(58) Field of Classification Search
  CPC ......... Y10T 29/49117; Y10T 29/49002; A61B 18/14; A61B 18/148; A61B 2017/0088; A61B 2218/002
  USPC .................. 29/848, 846, 829, 825, 592.1
  See application file for complete search history.

(56) References Cited

U.S. PATENT DOCUMENTS

| | | | |
|---|---|---|---|
| 8,597,288 B2* | 12/2013 | Christian | A61B 18/1492 606/41 |
| 2002/0049438 A1* | 4/2002 | Sharkey | A61B 18/1402 606/41 |
| 2006/0141861 A1* | 6/2006 | Darley | A61N 1/05 439/587 |
| 2011/0230799 A1 | 9/2011 | Christian et al. | |

FOREIGN PATENT DOCUMENTS

| | | |
|---|---|---|
| FR | 2 592 575 A1 | 7/1987 |
| WO | WO 95/05125 A2 | 2/1995 |

OTHER PUBLICATIONS

Oct. 30, 2015 Examination Report issued in European Patent Application No. GB1001645.9.

\* cited by examiner

ELECTROSURGICAL INSTRUMENT

This is a divisional application of U.S. patent application Ser. No. 13/011,512, filed Jan. 21, 2011 which is a non-provisional application of U.S. Application 61/300,068, filed Feb. 1, 2010, and which claims priority to Great Britain Application No. 1001645.9, filed on Feb. 1, 2010. The disclosure of the prior application is hereby incorporate by reference herein in its entirety.

This invention relates to an electrosurgical instrument for the treatment of tissue, and to a method of manufacturing such an instrument. Such electrosurgical instruments are commonly used for the vaporisation and/or coagulation of tissue in surgical intervention, most commonly in "keyhole" or minimally invasive surgery, but also in "open" surgery.

By its very nature, keyhole surgery requires very fine and precise instruments. However, these same instruments are often required to withstand very high temperatures, and must be manufactured such that the components making up the electrosurgical instrument are strong and robust so that the chances of parts of the instrument becoming detached during the surgical procedure are very small indeed. It has been known to over-mould the electrical components of an electrosurgical instrument with a silicone material for electrical insulation. However, silicone is insufficiently rigid or hard to reliably hold the electrical components in place on its own, such that the components do not become detached, and neither can it withstand high temperatures. The present invention attempts to provide a surgical instrument that can fulfil these demanding requirements.

Therefore, according to a first aspect of the invention, a method of manufacturing an electrosurgical instrument is provided including the steps of presenting an electrode, attaching a sacrificial portion to the electrode to form a first electrode assembly, moulding an insulating material over the first electrode assembly to form a second electrode assembly, and subjecting the second electrode assembly to a further process which is capable of removing the sacrificial portion without removing the insulating material, the sacrificial portion being removed to form at least one cavity within the electrosurgical instrument.

By moulding the insulating material over the electrode in situ, as opposed to manufacturing separate components and assembling them, very small and intricate designs can be realised and the integrity of the finished product is increased (i.e. the possibility of the components becoming separated during use is minimised).

The sacrificial portion is conveniently coated or moulded on to at least part of the electrode, prior to the addition of the ceramic insulating material. Typically, the sacrificial portion is formed of a plastics material, such as wax, silicone or a thermoplastic material such as polypropylene. The sacrificial material is designed so as to be removed during the manufacturing process, typically during the step of sintering the insulating material (where the insulating material is ceramic), or otherwise heating the material (where it is non-ceramic, or a material that does not require sintering). The sacrificial portion is capable of withstanding the moulding of the insulating material, in order to retain its structural integrity such that the insulating material is moulded over the sacrificial portion. However, where a ceramic insulating material is used, during the firing of the ceramic, when the temperatures can reach upwards of 1500° C., the sacrificial material is burnt away and removed. If a ceramic material is not used, then a heating step can be included to heat the electrode so as to deliberately burn away the sacrificial portion.

Where a ceramic material is used, the sintering of the ceramic insulating material can conveniently be carried out as a two stage process, with a first debinding stage followed by a second firing stage. The debinding stage is typically carried out at temperatures in the region of 250° C., and during this stage the binder material (if used) is removed by the applied heat. The second firing stage fuses the ceramic powder to form a solid component, and is typically carried out at temperatures in excess of 1500° C.

Whatever the material of the insulating material, the sacrificial portion is conveniently removed to form a cavity within the electrosurgical instrument. This cavity may conveniently be a space to allow for the introduction of another component, such as a lead or other electrical connection. Alternatively, the cavity may conveniently be a suction passage within the electrosurgical instrument, or other lumen capable of transmitting fluid or other materials to and from the distal end of the instrument.

The electrode conveniently includes a tissue treatment portion and a connection portion, and the insulating material is conveniently moulded into a component having a first portion and a second portion, with the first portion being moulded around the tissue treatment portion of the electrode, and the second portion moulded over the connection portion of the electrode. Thus the connection portion of the electrode is completely embedded in the second portion of the insulating material, but the first portion of the insulating material is moulded around the electrode portion so as to leave at least a part of it exposed for the treatment of tissue. The method preferably includes the step of injection moulding the insulating material over the electrode.

In one example embodiment the insulating material is a ceramic material, such as alumina or zircon toughened alumina (ZTA). There are several techniques for applying the ceramic material, including ceramic injection moulding (CIM), powder injection moulding of the ceramic, or pressing the ceramic to form the final shape. The ceramic material is moulded over the electrode when the ceramic is still in its unfired state. The ceramic material may conveniently be combined with a plastics material acting as a binder, to bind the powdered ceramic material into a mouldable state. The ceramic is then subjected to a further step, in which it is sintered to fuse the ceramic powder to form the finished ceramic material. This additional step of sintering the ceramic material is performed after it has been moulded over the electrode.

In another example embodiment the insulating material may be a suitably hard and/or rigid plastics material, such as PVDF (polyvinylidinefluoride), or PEEK (polyetheretherketone). In this respect, the chosen insulating material should be substantially rigid, such that the components of the electrode are held securely within the moulding without relative movement or the possibility of the components coming loose.

Many sufficiently hard and rigid insulating materials may be suitable for use in embodiments of the invention, provided that they are compatible for use in a surgical instrument (i,e. are generally inert, and non-toxic). In this respect, materials with a Shore A hardness of greater than 80 may be used. Even harder materials may more preferably be used, such as materials with a Shore D hardness in excess of 40, or more preferably in excess of 60 or 80. For example, PEEK has a typical Shore D hardness in excess of 80, and PVDF in excess of 40.

As stated previously, by embedding the electrode in the insulating material, and forming the combined components in situ, the electrosurgical instrument can be manufactured to be both small and complex, without requiring the complex assembly of multiple small parts, each of which thereby becoming a risk for disengagement and detachment during the surgical procedure.

The sacrificial portion is typically removed to form a suction passage through the tissue treatment portion of the electrode. In this way, debris or other materials in the vicinity of the electrode can be aspirated into the suction passage, and removed from the surgical site. Alternatively or additionally, the sacrificial portion is conveniently removed to form a suction lumen through the second portion of the insulating material. Thus, the suction passage is typically able to run from the tissue treatment portion of the electrode, through the insulating material alongside the connection portion of the electrode, and along the shaft of the instrument to exit the instrument at or near its proximal end. By using the sacrificial material to create the suction passage, the suction passage may if desired follow a complex path, unlike more conventional assembly techniques in which the suction passage is normally only a generally straight, longitudinally-extending tube.

According to a further aspect of the invention, an electrosurgical instrument is provided comprising an electrode, the electrode being embedded in an electrically insulating material moulded around the electrode, the electrosurgical instrument having at least one cavity, the cavity having been formed by the removal of a sacrificial material during a manufacturing process without removal of the surrounding insulating material.

The instrument is conveniently adapted so that the electrode assembly is capable of either the vaporisation or coagulation of tissue. In a first arrangement, electrosurgical instrument is designed to be operated in a conductive fluid, with the conductive fluid completing the current path between the electrodes of the electrode assembly. This means that the instrument operates to perform what is known as "underwater" electrosurgery, in which the conductive site is immersed in a conductive fluid such as saline, and the electrodes operate immersed in said conductive fluid. An example of this type of electrosurgical system is given in our earlier U.S. Pat. No. 6,004,319. The power and voltage settings used by the generator are such that the conductive fluid surrounding the electrodes is vaporised when the electrosurgical instrument is operated in its cutting mode.

Alternatively, the electrosurgical instrument is designed to be operated in a dry-field environment, with the electrodes of the electrode assembly being in direct contact with the tissue to be treated, and with the tissue completing the current path therebetween. An example of this type of electrosurgical system is given in our earlier U.S. Pat. No. 6,832,998. The power and voltage settings used by the generator are generally lower than in underwater electrosurgical systems, as the electrodes contact the tissue directly and there is no need to form a pocket of vaporised saline surrounding the electrode.

Figure 2:
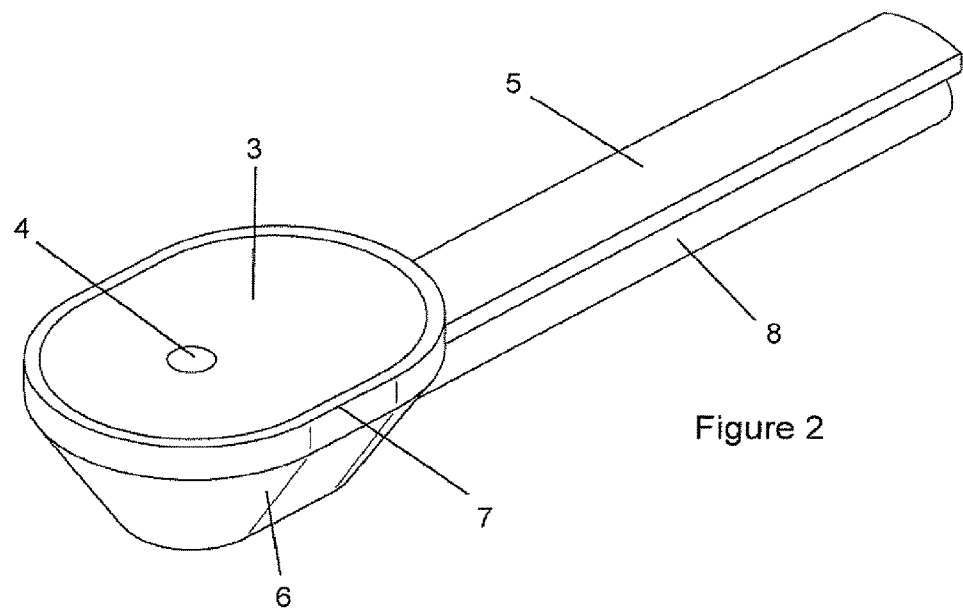
Figure 3:
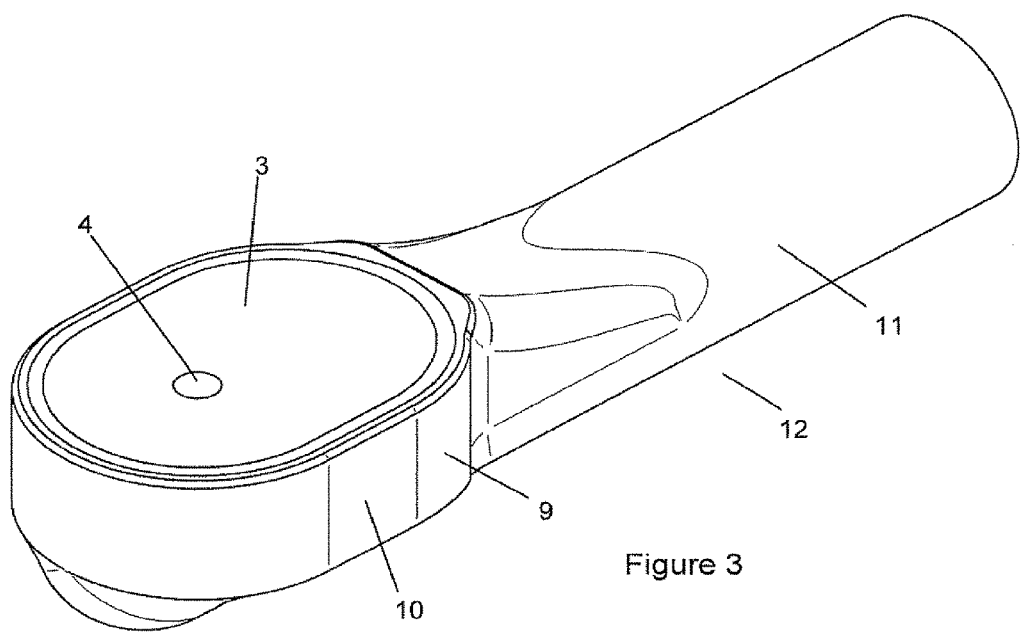
Figure 4:
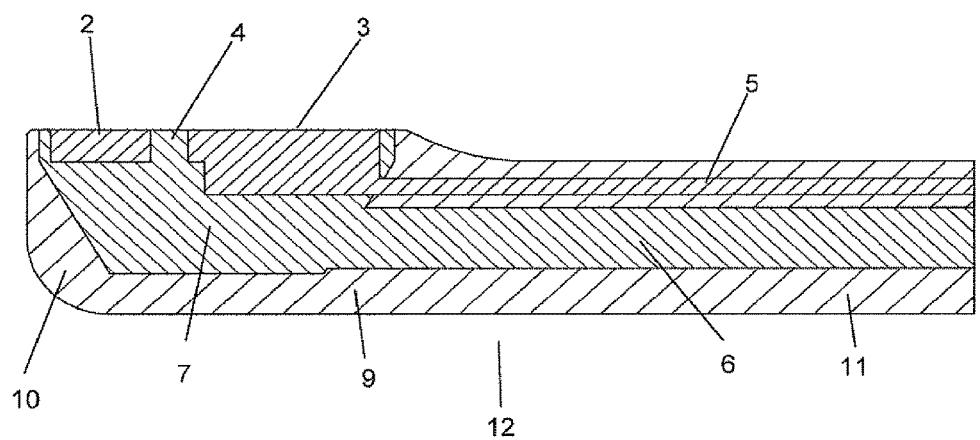
Figure 5:
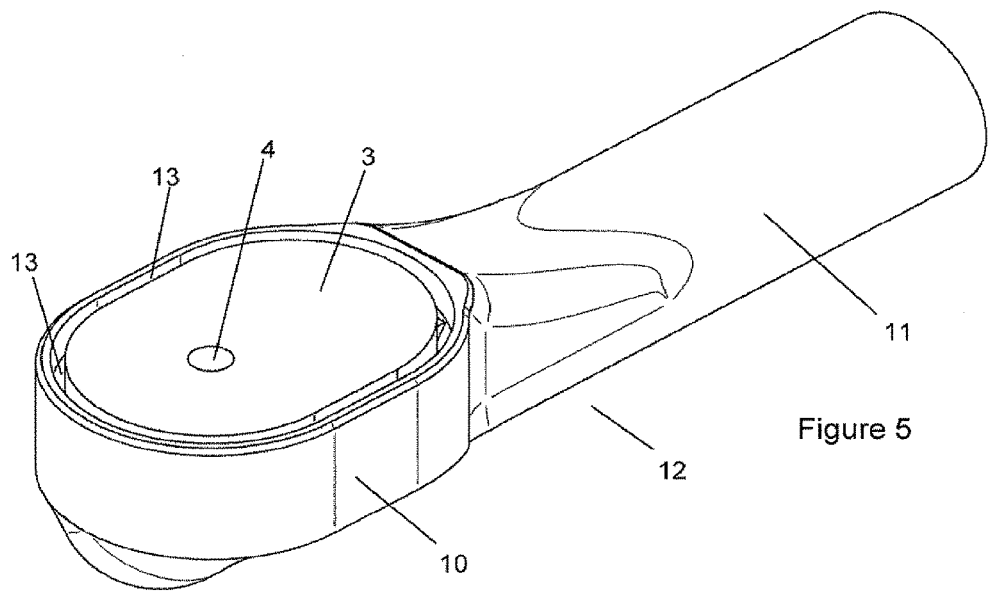
Figure 6:
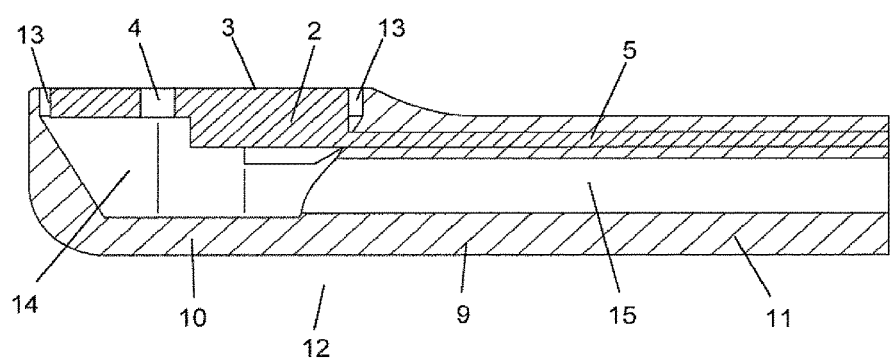

The invention will now be further described, by way of example only, with reference to the accompanying drawings, in which:

FIG. 1 is a perspective view of an electrode for use in an electrosurgical instrument manufactured in accordance with the present invention, FIG. 2 is a perspective view of the electrode of FIG. 1, shown in the second stage of the manufacturing process of the present invention, FIG. 3 is a perspective view of the electrode of FIG. 2, shown in the third stage of the manufacturing process of the present invention, FIG. 4 is a schematic cross-sectional view of the electrode of FIG. 3, FIG. 5 is a perspective view of the electrode of FIG. 3, shown in the final stage of the manufacturing process of the present invention, and FIG. 6 is a schematic cross-sectional view of the electrode of FIG. 5.

Referring to the drawings, FIG. 1 shows an electrode 1 forming the first part of an electrosurgical instrument manufactured in accordance with a first embodiment of the present invention. The electrode 1 comprises a tissue treatment portion 2 being generally planar in construction and including a tissue treatment face 3, and a suction aperture 4. The electrode 1 also includes a longitudinally extending connection portion 5 leading from the tissue treatment portion 2. The electrode 1 is integrally formed in FIG. 1, with the portions 2 and 5 being different parts of an integral structure. The electrode is formed of metal, typically tungsten or titanium.

FIG. 2 shows the next stage of the manufacturing process. The electrode is placed in a mould and a layer of sacrificial material 6 is moulded over the electrode. The sacrificial material comprises a first portion 7 surrounding the tissue treatment portion, and a second portion 8 lying alongside the connection portion 5 of the electrode. The sacrificial material 6 fills the suction aperture 4, but the first portion 7 does not cover the tissue treatment face 3, which remains exposed. However, as the sacrificial material is to be removed during a later step to be subsequently described, it may alternatively be applied to the tissue treatment face if desired. The sacrificial material is typically a thermoplastics material such as polypropylene, or alternatively wax or silicone can be used as the sacrificial material 6.

FIGS. 3 & 4 show the next stage of the manufacturing process. The electrode 1 and sacrificial material 6 is placed in a further mould and a powdered ceramic material 9 is moulded over the component of FIG. 2. The ceramic material 9 also comprises a first portion 10 and a second portion 11. The first portion 10 once again surrounds the tissue treatment electrode, but does not cover the tissue treatment face 3. The second portion 11 completely surrounds the connection portion 5 of the electrode and the second portion 8 of the sacrificial material. The ceramic material is typically alumina, possibly toughened with Zirconia. The first and second portions 10 & 11 of the ceramic material are integral with one another, to form a single continuous component 12.

The component 12 is then subjected to a two-stage sintering process. During the first stage, the component 12, still in the mould in which the powdered ceramic material has been added, is subjected to a thermal debinding treatment during which the component 12 is typically held at a temperature of 250° C. for a period of 3 hours. During this thermal treatment, the plastics binder used to hold the ceramic powder together in mouldable form is removed. Also, during this debinding treatment, the sacrificial material 6 is melted and burnt off, to leave cavities where the material 6 had previously been. Following this debinding treatment, the component 12 is removed from the mould and subjected to the second stage of the sintering process, which is a high temperature firing during which the component is held at an elevated temperature, typically 1500° C. for a period of 3 hours. This fuses the powdered ceramic material into a solid component, with the electrode 1 embedded within the ceramic material 9.

FIGS. 5 & 6 show the final component, with the electrode 1 embedded within the ceramic 9. The sacrificial material has been removed to leave a peripheral suction channel 13 around the circumference of the tissue treatment face 3. The sacrificial material has also been removed in other areas, creating a chamber 14 under the tissue treatment portion 2 of the electrode 1, and a suction lumen 15 extending from the chamber 14 through the second portion 11 of the ceramic material 9. The sacrificial material 6 has also been removed from the suction aperture 4, such that it presents an open passage through the tissue treatment face 3 and feeding into the chamber 14. In this way, debris adjacent the tissue treatment face 3 can be aspirated into the suction lumen 15, either through the aperture 4 or via the peripheral channel 13.

The component 12 can be attached to the shaft (not shown) of an electrosurgical instrument, or the connection portion 5 and second portion 11 of the ceramic material can be sufficiently long so as to constitute the shaft of the instrument. The electrosurgical instrument may be a monopolar instrument, in which case only the one electrode 1 is present on the instrument shaft. Alternatively, the electrosurgical instrument can be a bipolar or multi-polar instrument, in which case one or more further electrodes are provided on the shaft, either conventionally or embedded in the ceramic material as previously described.

The instrument is designed to be operated in a conductive fluid such as saline, with the fluid completing the circuit between the electrodes. However, the instrument can also be used as a dry-field instrument, in which case the user must ensure that the electrodes are placed in contact with the tissue to be treated.

Alternative embodiments will be envisaged by those skilled in the art without departing from the scope of the present invention. For example, as discussed previously, instead of using a ceramic material, in other embodiments another substantially rigid material may be used, such as PEEK, or PVDF. By embedding the electrode within such a rigid material, the electrode is held securely within the electrosurgical instrument, and the need for complex and potentially unreliable connecting mechanisms is avoided.

The invention claimed is:

1. A method of manufacturing an electrosurgical instrument comprising:
   presenting an electrode, the electrode including at least one through hole,
   attaching a sacrificial portion to the electrode to form a first electrode assembly, the sacrificial portion filling the at least one through hole,
   moulding an insulating material over the first electrode assembly to form a second electrode assembly, and
   subjecting the second electrode assembly to a heat treatment process, thereby melting the sacrificial portion without removing the insulating material such that the sacrificial portion is removed to form at least one cavity between the electrode and the insulating material, the cavity communicating with the at least one through hole to form a suction channel through the electrosurgical instrument.

2. The method according to claim 1, wherein the sacrificial portion is coated on to at least part of the electrode.

3. The method according to claim 1, wherein the sacrificial portion is moulded on to at least part of the electrode.

4. The method according to claim 1, wherein the sacrificial portion is formed of a plastics material.

5. The method according to claim 1, wherein the electrode includes a tissue treatment portion and a connection portion, the insulating material is moulded into a component having a first portion and a second portion, the first portion is moulded around the tissue treatment portion of the electrode, and the second portion is moulded over the connection portion of the electrode.

6. The method according to claim 1, wherein the moulding comprises injection moulding the insulating material over the electrode.

7. The method according to claim 1, wherein the insulating material is a ceramic material.

8. The method according to claim 7, further comprising sintering the ceramic material after it has been moulded over the electrode.

9. The method according to claim 8, wherein the sacrificial portion is removed during the sintering of the ceramic insulating material.

10. A method of manufacturing an electrosurgical instrument comprising:
    presenting an electrode, the electrode including at least one through hole,
    attaching a sacrificial portion to the electrode to form a first electrode assembly, the sacrificial portion filling the at least one through hole,
    moulding an insulating material over the first electrode assembly to form a second electrode assembly, and
    forming at least one cavity between the electrode and the insulating material by melting the sacrificial portion from the second electrode assembly without removing the insulating material, the cavity communicating with the at least one through hole to form a suction channel through the electrosurgical instrument.

* * * * *